United States Patent
Harada et al.

(10) Patent No.: US 11,685,652 B2
(45) Date of Patent: Jun. 27, 2023

(54) CHLORINE DIOXIDE GENERATION DEVICE AND CHLORINE DIOXIDE GENERATION SYSTEM

(71) Applicant: LUMICA CORPORATION, Fukuoka (JP)

(72) Inventors: Shiro Harada, Fukuoka (JP); Masaya Ito, Fukuoka (JP)

(73) Assignee: LUMICA CORPORATION, Fukuoka (JP)

( * ) Notice: Subject to any disclaimer, the term of this patent is extended or adjusted under 35 U.S.C. 154(b) by 45 days.

(21) Appl. No.: 17/604,937

(22) PCT Filed: Apr. 15, 2020

(86) PCT No.: PCT/JP2020/016532
§ 371 (c)(1),
(2) Date: Oct. 19, 2021

(87) PCT Pub. No.: WO2020/241097
PCT Pub. Date: Dec. 3, 2020

(65) Prior Publication Data
US 2022/0212930 A1    Jul. 7, 2022

(30) Foreign Application Priority Data

May 29, 2019   (JP) .............................. JP2019-100597

(51) Int. Cl.
  *C01B 11/02*   (2006.01)
  *A61L 9/04*   (2006.01)
  (Continued)

(52) U.S. Cl.
  CPC ............ *C01B 11/024* (2013.01); *A61L 9/048* (2013.01); *A61L 9/14* (2013.01); *A61L 2101/06* (2020.08); *A61L 2209/134* (2013.01)

(58) Field of Classification Search
None
See application file for complete search history.

(56) References Cited

U.S. PATENT DOCUMENTS

| 5,411,176 A | * | 5/1995 | Favre ................... B05B 11/026 |
|  |  |  | 222/137 |
| 8,562,907 B2 |  | 10/2013 | Green |

(Continued)

FOREIGN PATENT DOCUMENTS

| JP | H4-46003 A | 2/1992 |
| JP | H11-278808 A | 10/1999 |

(Continued)

OTHER PUBLICATIONS

International Search Report issued in PCT/JP2020/016532 dated Jun. 30, 2020 with English Translation (7 pages).

(Continued)

*Primary Examiner* — Jelitza M Perez
(74) *Attorney, Agent, or Firm* — Nakanishi IP Associates, LLC (57) ABSTRACT

Provided is a chlorine dioxide generation device, suitable for long-term storage, discharging a chlorine dioxide-generating mixture that remains at an object of interest when used to thereby stably exhibit the effect of chlorine dioxide. A chlorine dioxide generation device, comprising: a first container containing a first composition comprising a chlorite and fumed silica; a second container containing a second composition comprising an acidic substance and fumed silica; an outer container housing the first container and the second container; a mixing section that mixes the first composition released from the first container and the second composition released from the second container to produce (Continued)

a mixed composition; and a discharging section that discharges the mixed composition produced by mixing in the mixing section.

10 Claims, 2 Drawing Sheets

(51) Int. Cl.
*A61L 9/14* (2006.01)
*A61L 101/06* (2006.01)

(56) References Cited

U.S. PATENT DOCUMENTS

| | | | |
|---|---|---|---|
| 2007/0172412 | A1 | 7/2007 | Hratko et al. |
| 2013/0202484 | A1* | 8/2013 | Green ............... A01N 31/02 222/135 |

FOREIGN PATENT DOCUMENTS

| | | |
|---|---|---|
| JP | 2009-524572 A | 7/2009 |
| JP | 2012-36072 A | 2/2012 |
| JP | 2013-177282 A | 9/2013 |
| JP | 2013-540118 A | 10/2013 |
| JP | 2013-230974 A | 11/2013 |
| JP | 2017-24962 A | 2/2017 |
| JP | 2018-35016 A | 3/2018 |
| JP | 2018-80062 A | 5/2018 |

OTHER PUBLICATIONS

International Preliminary Report on Patentability (Chapter II of PCT) issued in PCT/JP2020/016532 dated Jun. 1, 2021, with English Translation (6 pages).

* cited by examiner

CHLORINE DIOXIDE GENERATION DEVICE AND CHLORINE DIOXIDE GENERATION SYSTEM

TECHNICAL FIELD

The present invention relates to a chlorine dioxide generation device and a chlorine dioxide generation system.

BACKGROUND ART

There has been a demand for products for sanitization, disinfection, sterilization, deodorization and epidemic prevention that eliminate microorganisms and viruses floating or adhering to spaces, objects and living organisms. As the products used for such sanitization or the like, products such as stationary-type products, stick-type products and spray-type products that utilize chlorine dioxide have been put into practical use.

Patent Literature 1 discloses a method for producing a stabilized aqueous solution of chlorine dioxide characterized by: adding a buffer to an aqueous solution containing 3 to 15% of a chlorite to adjust the pH to 7 to 9; and then keeping the aqueous solution at a temperature of 20 to 50° C. for one to five days to obtain an aqueous solution having a desired concentration of chlorine dioxide.

Patent Literature 2 discloses a pure chlorine dioxide liquid formulation characterized by having dissolved chlorine dioxide gas, a chlorite and a pH adjuster as constituents.

Patent Literature 3 discloses a gel-like composition characterized by containing: a pure chlorine dioxide liquid formulation having dissolved chlorine dioxide gas, a chlorite and a pH adjuster as constituents; and a highly water-absorbent resin, wherein the pH adjuster is phosphoric acid or a salt thereof.

Patent Literature 4 discloses a hand sanitizer comprising (a) a first liquid component that comprises a chlorite solution and that is charged into a first dispenser and discharged therefrom as a first spray of the liquid component or as a first jet of the liquid component; and (b) a second liquid component that comprises an acid solution and that is charged into a second dispenser and discharged therefrom as a second spray of the liquid component or as a second jet of the liquid component, characterized in that mixing of the first liquid component and the second liquid component allows the chlorite and the acid to react to generate chlorine dioxide; a mixture of equal amounts of the first liquid component and the second liquid component contains at least 15% by mass of alcohols; and at least a part of the alcohols includes 3-methoxy-3-methylbutane-1-ol (MMB).

CITATION LIST

Patent Literature

Patent Literature 1: Japanese Patent Laid-Open No. 4-46003
Patent Literature 2: Japanese Patent Laid-Open No. 11-278808
Patent Literature 3: Japanese Patent Laid-Open No. 2013-230974
Patent Literature 4: Japanese Patent Laid-Open No. 2013-540118

SUMMARY OF INVENTION

Technical Problem

The chlorine dioxide liquid formulations comprising chlorine dioxide and the like are known as disclosed in Patent Literatures 1 to 3. As studied for the stabilization of chlorine dioxide also in these Patent Literatures, chlorine dioxide has low stability as it is, and is not suitable for long-term storage. In addition, chlorine dioxide, even if subjected to stabilization or other treatments, erodes containers or vaporizes or the like during storage, which results in a reduction in the chlorine dioxide concentration, or the like, and therefore, one-component chlorine dioxide liquid formulations is not suitable for long-term storage in some cases.

In Patent Literature 4, the chlorous acid solution is charged into the first dispenser, and the acid solution is charged into the second dispenser. However, if it was used in a liquid state as it is, in some cases, it quickly volatilized or flew down from the area where it adhered, and the like, and the effect was lost in a short time. Further, even if only a gelling agent such as a polymer was added, problems were sometimes caused with the stability of the gelling agent to chlorine dioxide or the like and the ease of use of the gelled solution.

In such situations, it is an object of the present invention to provide a chlorine dioxide generation device or a chlorine dioxide generation system, suitable for long-term storage, discharging a mixture generating chlorine dioxide that remains at an object of interest when used to thereby stably exhibit the effect of chlorine dioxide.

Solution to Problem

As a result of diligent research to solve the above problems, the present inventor has found that the invention described below meets the above object, and thus has completed the present invention. That is, the present invention relates to the invention described below.

<1> A chlorine dioxide generation device, comprising: a first container containing a first composition comprising a chlorite and fumed silica; a second container containing a second composition comprising an acidic substance and fumed silica; an outer container housing the first container and the second container; a mixing section that mixes the first composition released from the first container and the second composition released from the second container to produce a mixed composition and a discharging section that discharges the mixed composition produced by mixing in the mixing section.

<2> The chlorine dioxide generation device according to <1>, wherein: the first container and the second container are bag-shaped; the outer container is a pressure-resistant container that houses the first container and the second container and is filled with a propellant; the mixing section is a joint section of piping connected to the first container housed in the pressure-resistant container and piping connected to the second container housed in the pressure-resistant container; the chlorine dioxide generation device comprises an on-off valve for adjusting the release of the first composition and the second composition to the mixing section and the discharging section; and the mixed composition is injected from the discharging section by opening the on-off valve.

<3> The chlorine dioxide generation device according to <1> or <2>, wherein the fumed silica is a hydrophobic fumed silica.

<4> The chlorine dioxide generation device according to any of <1> to <3>, wherein the chlorite is one or more selected from the group consisting of sodium chlorite, potassium chlorite and calcium chlorite, and the first composition contains water and an alcohol as dispersion media.

<5> The chlorine dioxide generation device according to any of <1> to <4>, wherein the acidic substance is one or more selected from the group consisting of citric acid, phosphoric acid, acetic acid and hydrochloric acid, and the second composition contains water and an alcohol as dispersion media.

<6> The chlorine dioxide generation device according to any of <1> to <5>, wherein a pH of the first composition is 9 or more.

<7> The chlorine dioxide generation device according to any of <1> to <6>, wherein the first composition contains one or more selected from the group consisting of sodium hydroxide, potassium hydroxide, lithium hydroxide, calcium hydroxide, magnesium hydroxide, sodium carbonate and sodium tetraborate.

<8> The chlorine dioxide generation device according to any of <1> to <7>, wherein a pH of the second composition is 5 or less.

<9> A chlorine dioxide generation device, comprising a first composition comprising a chlorite and fumed silica and a second composition comprising an acidic substance and fumed silica, wherein: the chlorine dioxide generation device comprises: an inner container containing any one composition of the first composition and the second composition; and an outer container containing the other composition that is not contained in the inner container, the inner container being included in the outer container; and the chlorine dioxide generation device comprises: a mixing section that mixes the one composition released from the inner container and the other composition contained in the outer container to produce a mixed composition; and a discharging section that discharges the mixed composition produced by mixing in the mixing section.

<10> A chlorine dioxide generation system, comprising a first composition comprising a chlorite and fumed silica and a second composition comprising an acidic substance and fumed silica, wherein chlorine dioxide is generated from a mixed composition produced by mixing the first composition and the second composition.

Advantageous Effects of Invention

The chlorine dioxide generation device and the chlorine dioxide generation system of the present invention are suitable for long-term storage and discharges a chlorine dioxide-generating mixture that remains at an object of interest when used to thereby stably exhibit the effect of chlorine dioxide.

DESCRIPTION OF EMBODIMENTS

Hereinafter, modes for carrying out the present invention will be described in detail. The description of the constituent elements described below is one example (representative example) of the embodiment of the present invention, and the present invention is not limited to the following contents unless the gist thereof is changed. When the numerical range is represented by using the expression " . . . to . . . " in the present specification, it is used as an expression including numerical values before and after "to".

[Chlorine Dioxide Generation Device of the Present Invention]

The first chlorine dioxide generation device of the present invention comprises: a first container containing a first composition comprising a chlorite and fumed silica; a second container containing a second composition comprising an acidic substance and fumed silica; an outer container housing the first container and the second container; a mixing section that mixes the first composition released from the first container and the second composition released from the second container to produce a mixed composition; and a discharging section that discharges the mixed composition produced by mixing in the mixing section.

The second chlorine dioxide generation device of the present invention comprises a first composition comprising a chlorite and fumed silica and a second composition comprising an acidic substance and fumed silica; an inner container containing any one composition of the first composition and the second composition, and an outer container containing the other composition that is not contained in the inner container, the first container being included in the outer container; and a mixing section that mixes the one composition released from the inner container and the other composition contained in the outer container to produce a mixed composition; and a discharging section that discharges the mixed composition produced by mixing in the mixing section.

In the present application, the first chlorine dioxide generation device of the present invention and the second chlorine dioxide generation device of the present invention are collectively referred to as the chlorine dioxide generation device of the present invention. The chlorine dioxide generation device of the present invention is suitable for long-term storage, and a discharged mixture remains at an object of interest when used to stably generate chlorine dioxide.

[Chlorine Dioxide Generation System of the Present Invention]

The chlorine dioxide generation system of the present invention comprises a first composition comprising a chlorite and fumed silica and a second composition comprising an acidic substance and fumed silica, wherein chlorine dioxide is generated from a mixed composition produced by mixing the first composition and the second composition. The chlorine dioxide generation system of the present invention is suitable for long-term storage by storing the first composition and the second composition separately from each other, and stably generates chlorine dioxide by mixing and using the first composition and the second composition when used to produce a mixed composition and thereby allowing the mixed composition to remain at an object of interest. The chlorine dioxide generation system of the present invention can be used in the chlorine dioxide generation device of the present invention, and configurations common to each other can be mutually incorporated.

First Embodiment

Figure 1:
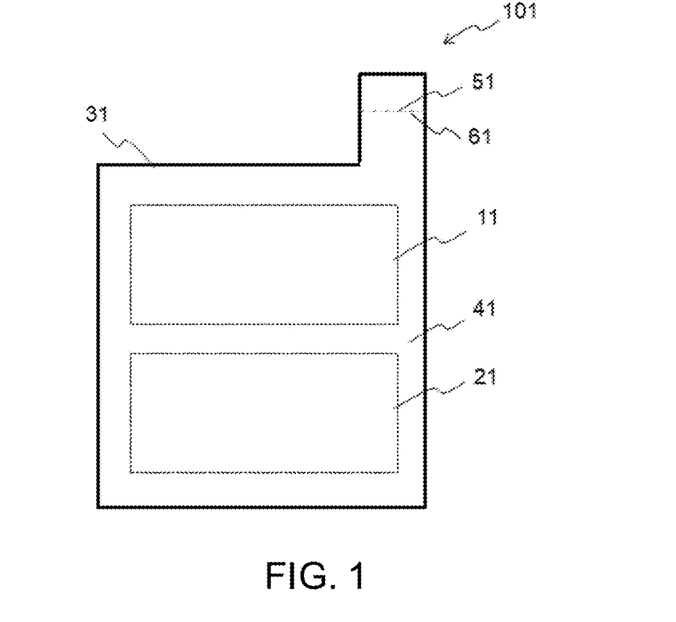
FIG. 1 is a schematic diagram showing the first embodiment of a chlorine dioxide generation device according to the present invention.

FIG. 1 is a schematic diagram showing the first embodiment of a chlorine dioxide generation device according to the present invention. The chlorine dioxide generation device 101 comprises a first container 11 and a second container 21, and these containers are housed in an outer container 31. The inside of the outer container 31 is a mixing section 41, and a discharging section 51 is opened by cutting a notch 61.

[First Container 11]

The chlorine dioxide generation device 101 comprises a first container 11. The first container 11 is a container containing a first composition. The first composition comprises a chlorite and fumed silica. The first container 11 to be used can be, for example, a bag-shaped container having closed four sides. The first container 11 is sealed so that the first composition does not leak from the inside of the first container 11 when the chlorine dioxide generation device 101 is stored.

Further, the first container 11 has a structure provided with a portion that is easily opened by breaking it or the like so that the first composition is released when the chlorine dioxide generation device 101 is used. The portion that is easily opened by breaking it can be provided, for example, by providing a portion having a weak heat-sealing property, providing a portion having a thin thickness or providing a region having a narrow adhesive portion. In addition, the first container 11 is formed of a material that is stable even when in contact with the first composition containing a chlorite, fumed silica and a dispersion medium therefor (such as water or an alcohol). For example, a bag made of a sheet of polyolefin such as polyethylene or polypropylene can be used.

[Second Container 21]

The chlorine dioxide generation device 101 has a second container 21. The second container 21 is a container containing a second composition. The second container 21 contains a second composition comprising an acidic material and fumed silica. The other configurations of the second container 21 may be similar to those of the first container 11, except that it contains the second composition instead of the first composition. The second container 21 to be used can be, for example, a bag-shaped container having closed four sides. The second container 21 is sealed so that the second composition does not leak from the inside of the second container 21 when the chlorine dioxide generation device 101 is stored.

Further, the second container 21 has a structure provided with a portion that is easily opened by breaking it or the like so that the second composition is released when the chlorine dioxide generation device 101 is used. In addition, the second container 21 is formed of a material that is stable even when in contact with the second composition containing an acidic substance, fumed silica and a dispersion medium therefor (such as water or an alcohol). For example, a bag made of a sheet of polyolefin such as polyethylene or polypropylene can be used.

[Outer Container 31]

The chlorine dioxide generation device 101 has an outer container 31. The outer container 31 is a container housing a first container 11 and a second container 21. The outer container 31 may be provided with a convex portion for forming a discharging section 51 and may be in the shape of a closed bag except for the convex portion. The outer container 31 is formed of a material that is stable even when in contact with the components constituting the first composition and the second composition, and chlorine dioxide generated by the reaction thereof, and the like. For example, a bag made of a sheet of polyolefin such as polyethylene or polypropylene can be used.

[Mixing Section 41]

The mixing section 41 is a region where the first composition and the second composition are mixed. In the chlorine dioxide generation device 101, the region that is around the first container 11 and the second container 21 and inside the outer container 31 serves as the mixing section 41. When used, the outer container 31 is pressed or the like from the outside to break or the like a part of the first container 11 and a part of the second container 21 due to a change in internal pressure, and the first composition is released from the first container 11 into the outer container 31 and the second composition is released from the second container 21 into the outer container 31. The first composition and the second composition released from the first container and the second container, respectively, are mixed in the outer container 31 to produce a mixed composition.

[Discharging Section 51]

The discharging section 51 is a section that discharges a mixed composition. When the notch 61 provided in the convex portion of the outer container 31 is torn, an opening is provided in the outer container 31, and this opening becomes the discharging section 51. The mixed composition produced by mixing in the mixing section 41 is discharged from the discharging section 51. The mixed composition comprises a chlorite and an acidic substance, which react to produce a composition that generates chlorine dioxide. Chlorine dioxide can be thereby generated at any area to which the mixed composition is adhered.

Second Embodiment

Figure 2:
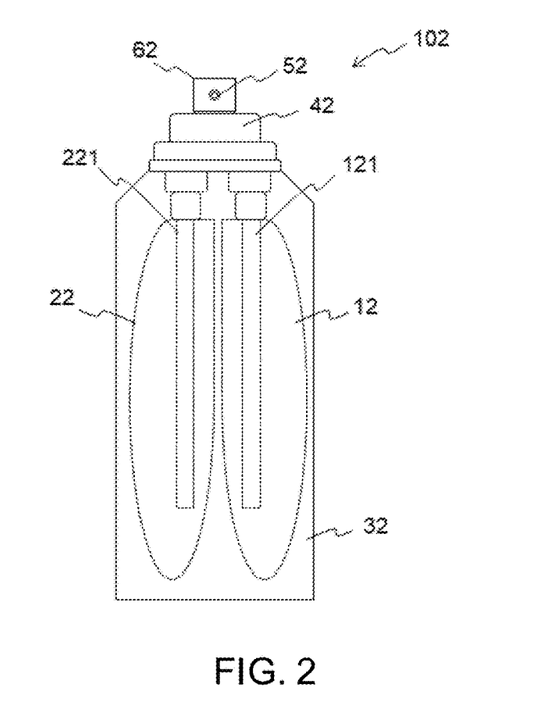
FIG. 2 is a schematic diagram showing the second embodiment of a chlorine dioxide generation device according to the present invention.

FIG. 2 is a schematic diagram showing the second embodiment of a chlorine dioxide generation device according to the present invention. The chlorine dioxide generation device 102 comprises a first container 12 and a second container 22, and these containers are housed in an outer container 32. The outer container 32 is filled with a propellant, and pressure is applied to the first container 12 and the second container 22. The first container 12 has piping 121 connected inside, the second container 22 has piping 221 connected inside, and the piping 121 and the piping 221 have structures in which the internal spaces can be in communication with each other at a joint section when a button 62 is pressed. When the button 62 is not pressed, the joint section is in a closed state, and the piping 121 and the piping 221 are separated from each other. When the button 62 is pressed, the piping 121 and the piping 221 becomes in communication with each other at the mixing section, the composition contained in the first container 12 and the composition contained in the second container 22 are extruded by the pressure of a propellant, and a mixed composition produced by mixing both compositions is discharged from the discharging section.

[First Container 12]

The first container 12 is bag-shaped and contains a first composition. The first container 12 is housed in an outer container 32. The first container 12 has piping 121 arranged therein and the piping 121 is connected to a mixing section 42 at the inside thereof. When a button 62 is not pressed, the joint portion between the piping 121 and piping 221 in the mixing section 42 is in a closed state, and the spaces in the first container 12 and the piping 121 containing the first composition are separated from other spaces such as that in a second container 22.

In addition, the first container 12 is formed of a material that is stable even when in contact with the first composition containing a chlorite, fumed silica and a dispersion medium therefor (such as water or an alcohol) and a material that is stable to the pressure inside the outer container 32 and flexible. For example, a bag made of a sheet of polyolefin such as polyethylene or polypropylene can be used.

[Second Container 22]

The second container 22 is bag-shaped and contains a second composition. The second container 22 is housed in an outer container 32. The second container 22 has piping 221 arranged therein and the piping 221 is connected to a mixing section 42 at the inside thereof. When the button 62 is not pressed, the joint portion between the piping 121 and piping 221 in the mixing portion 42 is in a closed state, and the spaces in the second container 22 and the piping 221 containing the second composition are separated from other spaces such as that in the first container 12.

In addition, the second container 22 is formed of a material that is stable even when in contact with the second composition containing a chlorite, fumed silica and a dispersion medium therefor (such as water or an alcohol) and a material that is stable to the pressure inside the outer container 32 and flexible. For example, a bag made of a sheet of polyolefin such as polyethylene or polypropylene can be used.

[Outer Container 32]

The outer container 32 is a container housing the first container 12 and the second container 22 or the like. The outer container 32 is filled with a propellant around the first container 12 and the second container 22. By filling the outer container 32 with the propellant, the pressure inside the outer container 32 becomes positive. When the button 62 is pressed to open the flow path to the discharging section 52, the compositions contained in the first container 12 and the second container 22 are mixed and injected. The outer container 32 is a pressure-resistant container that can withstand such a high pressure. For example, this pressure-resistant container can be a metal container or be formed of a resin having a high strength or the like. The pressure-resistant container may also be a container having a multilayer structure as appropriate.

The propellant to be used can be a compressed gas. The compressed gas is used widely, and any relatively safe gas can be used as appropriate. For example, a nitrogen gas, a carbon dioxide gas, a nitrous oxide gas and a mixed gas thereof are used. As a guideline, the pressure inside the pressure-resistant container filled with the propellant can be, for example, approximately 0.3 to 1.2 MPa as the pressure at ordinary temperature of 25° C.

[Mixing Section 42, Discharging Section 52, Button 62]

The mixing section 42 has a joint section, in the inside thereof, in which piping 121 and piping 221 are connected and joined. The first composition released through piping 121 and the second composition released through piping 221 are mixed at this joint portion and discharged from a discharging section 52. The piping to the joint portion in the mixing section 42 may have an on-off valve that adjusts the injection, such as a check valve (not shown) that is closed due to the internal pressure of the composition to be released, the spring structure or the like. When the button 62 is open, the check valve is closed by the pressure from each container and the piping 121 and the piping 221 is separated, so that the first composition and the second composition can be prevented from being mixed and discharged from the discharging section 52. When the button 62 is pressed, the check valve is opened, the piping 121 and the piping 221 are connected, so that the first composition and the second composition are mixed at the connecting section and injected from the discharging section 52.

The button 62 is a button, provided on the mixing section 42, that is in a raised state by an internal pressure, a spring or the like when opened without being pressed and that is intended to adjust the on-off valve in the mixing section 42, such as to open the check valve, by being pressed when used. The discharging section 52 is an opening that is connected to piping 121, piping 221 and a connecting section thereof. When the button 62 is pressed to open the on-off valve, the mixed composition is injected from the discharging section 52.

The chlorine dioxide generation device 102 can have a structure utilizing the structure of a two-component mixed aerosol product. For example, a two-component mixed aerosol product disclosed in Japanese Patent Laid-Open No. 2016-160186 can be appropriately used as a reference.

The mixed composition produced by mixing in the mixing section 41 is discharged. The mixed composition contains a chlorite and an acidic substance, which react to produce a composition that generates chlorine dioxide. Chlorine dioxide can be thereby generated at any area to which the mixed composition is adhered.

Third Embodiment

Figure 3:
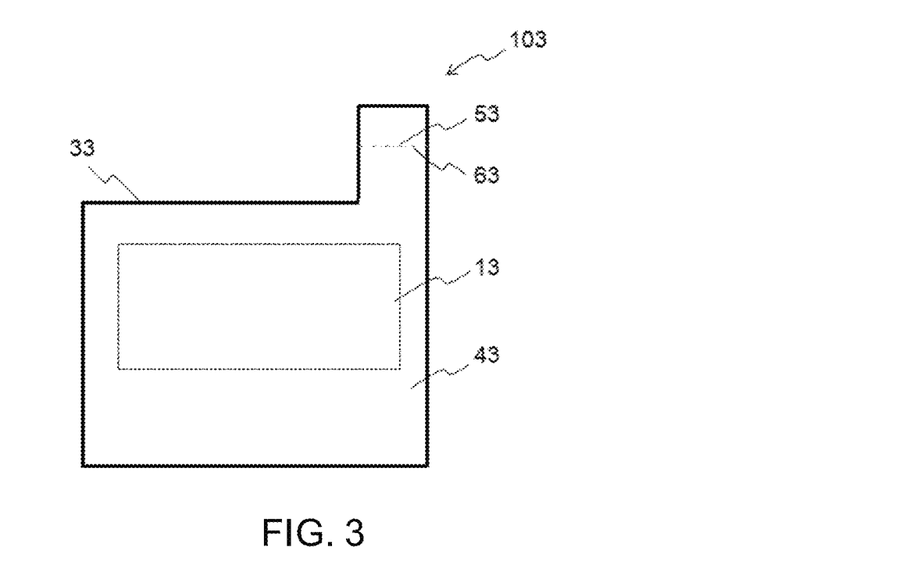
FIG. 3 is a schematic diagram showing the third embodiment of a chlorine dioxide generation device according to the present invention.

FIG. 3 is a schematic diagram showing the third embodiment of a chlorine dioxide generation device according to the present invention. The third embodiment is an embodiment of a second chlorine dioxide generation device according to the present invention. The chlorine dioxide generation device 103 has the inner container 13 housed in the outer container 33. The inside of the outer container 33 is a mixing section 43, and a discharging section 53 is opened by cutting a notch 63. The chlorine dioxide generation device 103 has a structure similar to that of the chlorine dioxide generation device 101 according to the first embodiment, but it has an inner container 13 instead of the first container 11, does not have the second container 21, has the outer container 33 instead of the outer container 31, and has the second composition directly contained in the outer container 33.

The chlorine dioxide generation device 103 has the inner container 13. The inner container 13 contains a first composition. The inner container 13 is similar to the first container 11, and the first container 11 can be used as the inner container 13.

In the chlorine dioxide generation device 103, the second composition contained in the second container 21 in the chlorine dioxide generation device 101 is contained in the outer container 33. Further, the first composition and the second composition are separated from each other by the inclusion of the inner container 13 in the outer container 33. The second composition contained in the second container 21 can be used as the second composition contained in the outer container 33.

The outer container 33 is a container containing a first composition and a second composition. In the chlorine dioxide generation device 103, the outer container 33 houses the inner container 13 containing the first composition and contains the second composition. That is, the outer container 33 can have the same structure as the outer container 31 except that it does not have the second container 21 of the chlorine dioxide generation device 101 and directly contains the second composition.

In the chlorine dioxide generation device 103, the region that is around the inner container 13 and inside the outer container 33 serves as a mixing section 43 in which the first composition and the second composition are mixed. At the time of use, the outer container 3 is pressed or the like from the outside to break or the like a part of the inner container 13 due to a change in internal pressure or the like and to thereby release the first composition from the inner container 13, and the first composition is mixed with the second composition in the outer container 33 to produce a mixed composition.

When the notch 63 provided in the convex portion of the outer container 33 is torn, an opening is provided in the outer container 33, and this opening becomes the discharging section 53. The mixed composition produced by mixing in the mixing section 43 is discharged. The mixed composition contains a chlorite and an acidic substance, which react to produce a composition that generates chlorine dioxide. Chlorine dioxide can be thereby generated at any area to which the mixed composition is adhered.

The chlorine dioxide generation device 103 according to the third embodiment include, as an example, a chlorine dioxide generation device in which the first composition is contained in an inner container. However, the second chlorine dioxide generation device of the present invention includes a chlorine dioxide generation device in which the second composition is contained in the inner container and the first composition is contained in the outer container 33 around the inner container and chlorine dioxide can be thereby generated at any area to which the mixed composition is adhered. The inner container containing the second composition may be similar to the second container 21.

These chlorine dioxide generation devices 101 to 103 are suitable for long-term storage because a chlorite and an acidic substance are separated from each other during storage of the devices, so that they are not allowed to easily react and chlorine dioxide is not generated. Further, the first composition and the second composition contain fumed silica, and each of the compositions is a gel-like composition. When the chlorine dioxide generation devices 101 to 103 are used, the mixed composition produced by mixing the first and second compositions is also in the form of gel. Since any of the first and second compositions and the mixed composition are also in the form of a gel, they are easily mixed homogeneously. In addition, the mixed composition can be adhered to any area in the form of gel and is held on or in remains at an object of interest when used to thereby stably exhibit the effect of chlorine dioxide.

[First Composition]

The chlorine dioxide generation device and the chlorine dioxide generation system of the present invention use the first composition comprising a chlorite and fumed silica. Chlorine dioxide is generated when used by the reaction of the chlorite with an acidic substance in the second composition. Further, by containing a pH adjuster, the color tone is not easily changed during storage and is stable. In addition, the first composition is alone in the form of gel, while the mixed composition produced by mixing it with the second composition used in the present invention is also in the form of gel and adheres to an object of interest in the form of gel to exhibit the effect of chlorine dioxide for a prolonged time.

[Chlorite]

The first composition comprises a chlorite. As the chlorite used in the first composition, a chlorite that generates chlorine dioxide by mixing it with the second composition can be used alone or in combination as appropriate. The chlorite that can be used includes one or more selected from the group consisting of sodium chlorite, potassium chlorite and calcium chlorite. Sodium chlorite and potassium chlorite are particularly suitable because of their ease of handling.

The concentration of the chlorite in the first composition can be appropriately set in consideration of the degree to which chlorine dioxide is generated during use. For example, the mass ratio of the chlorite to the entire first composition (the mass of the chlorite/the mass of the first composition) can be approximately 0.1 to 12% by mass. Preferably, it may be 0.5 to 10% by mass, 1 to 8% by mass, or 2 to 5% by mass.

[Fumed Silica]

The first composition comprises fumed silica. The second composition also comprises fumed silica.

Fumed silica is silicon dioxide produced by thermal decomposition, and it is produced by subjecting an evaporable silicon compound such as silicon tetrachloride to combustion and hydrolysis, for example, in a mixture of hydrogen and oxygen. Therefore, the fumed silica has silanol groups on its surface and generally exhibit hydrophilicity. Examples of such fumed silica that can be used include Aerosil (registered trademark) available from NIPPON AEROSIL CO., LTD. and Fumed Silica HDK (registered trademark) available from WACKER ASAHIKASEI SILICONE CO., LTD. Further, fumed silica is excellent in stability in the first composition and the second composition because it is an inorganic substance.

Fumed silica functions as a thickener, and the first composition, the second composition and mixtures thereof become gel-like by containing fumed silica.

The fumed silica to be used is preferably hydrophobic fumed silica. Hydrophobic fumed silica is fumed silica produced by chemically treating common hydrophilic fumed silica with silane or siloxane, and it exhibits hydrophobicity by the chemical bonding of a treatment agent to an oxide on the surface of the common fumed silica. For example, Aerosil (registered trademark) that is hydrophobic fumed silica manufactured by NIPPON AEROSIL CO., LTD., or the like is commercially available as hydrophobic fumed silica. Hydrophobic fumed silica does not easily react with a chlorite and an acidic substance, and is particularly excellent in stability during storage.

The proportion of fumed silica comprised in the first composition can be appropriately set in consideration of the degree of gelation during storage and use, or the like. For example, the mass ratio of fumed silica to the entire first composition (the mass of fumed silica/the mass of the first composition) can be approximately 0.5 to 30% by mass. This lower limit may be preferably 1% by mass or more or 2% by mass or more. This upper limit may be 25% by mass or less or 20% by mass or less, depending on the gel-like viscosity thereof or the like due to the other components in the composition or the like. It is may be 15% by mass or less or 10% by mass or less because gelation easily occurs by using hydrophobic fumed silica or the like in combination with an alcohol described later or by adjusting the pH.

[Dispersion Medium]

The first composition comprises a chlorite and fumed silica, which are dispersed in a dispersion medium. In the context of the present application, a chlorite, an acidic substance, fumed silica, a pH adjuster and the like are in a dissolved state or are in a dispersed state without being completely dissolved, depending on the temperature and concentration used. However, the dispersion includes dissolution and the dispersion medium includes those that function as a solvent, because they can generate chlorine dioxide in either state, in terms of storage and use.

The dispersion medium that can be used is one that is liquid at ordinary temperature, such as water or an organic solvent. In particular, the dispersion medium used is preferably a highly polar liquid such as water or an alcohol, in order to ionize or charge active ingredients as appropriate as to allow them to easily react. For the composition of the dispersion medium, any one of the above liquids may be used alone, but water and an alcohol is preferably used in combination.

In the case of a dispersion medium containing water, the lower limit of the proportion of the mass of water in the entire dispersion medium (the mass of water/the mass of the dispersion medium) is preferably 20% by mass or more and more preferably 30% by mass or more. Then, the upper limit may be 90% by mass or less, 80% by mass or less or 70% by mass or less. The balance can be another dispersion medium such as an alcohol. The water to be used can be purified water or clean water.

The dispersion medium preferably also includes an alcohol. In the case of a dispersion medium containing an alcohol, the lower limit of the proportion of the mass of an alcohol in the entire dispersion medium (the mass of water/the mass of the dispersion medium) is preferably 10% by mass or more, more preferably 20% by mass or more or further more preferably 30% by mass or more. Then, the upper limit may be 80% by mass or less or 70% by mass or less. The balance can be another dispersion medium such as water. In particular, when hydrophobic fumed silica is used, the use of water alone may reduce the dispersibility and/or may result in a very high concentration of the hydrophobic fumed silica for gelation, but the inclusion of an alcohol provides an excellent dispersibility and causes gelation to easily occur. Examples of the alcohol that can be suitably used include lower alcohols such as methyl alcohol, ethyl alcohol, butyl alcohol and propyl alcohol. In particular, isopropyl alcohol (IPA) is preferably used in consideration of safety and the like, because the chlorine dioxide generation device may be sometimes used around a human and animals and is used in combination to improve the dispersibility and the like of hydrophobic fumed silica.

[pH]

The first composition may comprise a chlorite, fumed silica and a dispersion medium. In addition, it may contain a pH adjuster or the like. The first composition preferably has a pH of 8 or higher, more preferably 9 or higher, and further more preferably 9.5 or higher, pH 9.8 or higher and pH 10.0 or higher. When protons are released from the components in the first composition, protons may react with a chlorite to generate chlorine dioxide. However, raising the pH can prevent such unintended generation of chlorine dioxide and it makes the chlorine dioxide generation device suitable for long-term storage.

The first composition preferably contains one or more components selected from the group consisting of sodium hydroxide, potassium hydroxide, lithium hydroxide, calcium hydroxide, magnesium hydroxide, sodium carbonate and sodium tetraborate. The inclusion of these components can prevent, if any, protons released from the components of the first compositions from reacting with a chlorite to generate chlorine dioxide. These components may be appropriately mixed and used in combination. The concentration of these components contained in the entire first composition (the amount of the components/the total amount of the first composition) can be 0.005% by mass or more, 0.01% by mass or more or 0.02% by mass or more. Then, the upper limit may be 5.0% by mass or less, 3.0% by mass or less or 2.0% by mass or less. These components can be pH adjusters used for adjusting the pH as described above, and may be appropriately mixed in combination at concentrations that gives a predetermined pH.

The first composition is preferably in the form of gel at least at ordinary temperature and ordinary pressure. The gelation of the first composition makes it possible to easily mix the first composition with the second composition beyond the difference therebetween in physical properties such as viscosity. In addition, the mixed composition produced by mixing them becomes a gel-like composition so that it adheres to any area and does not easily flow. For the first composition, the lower limit of the viscosity at 25° C. may be 1,000 mPa·s or more or 5,000 mPa·s or more, for example, as measured by a rotational viscometer. If the viscosity is too high, mixing may be not easily carried out or discharging or injection may not be easily carried out. Therefore, the upper limit may be 1,000 Pa·s or less or 500 Pa·s or less.

The viscosity can be measured, for example, using a rotary viscometer manufactured by Brookfield with a spindle: LV-4, a rotational speed: 0.3 RPM and a measurement temperature: 25° C.

The first composition may comprise the other component(s). For example, it may comprise a colorant to clarify where it has been used or a stabilizer, a preservative, a moisturizer or the like. In general, if it comprises a polymer-based thickener having a thickening effect, the thickener may react with a chlorite during storage to generate chlorine dioxide or may cause strings to be drawn from a discharging section (stringiness) when used. Therefore, the polymer-based thickener may be used with an upper limit of 2% by mass or less, 1% by mass or less, 0.5% by mass or less, 0.1% by mass or less or the like, so that it may not be substantially contained not to cause these problems.

[Second Composition]

The chlorine dioxide generation device and the chlorine dioxide generation system of the present invention use the second composition comprising an acidic substance and a fumed silica. Chlorine dioxide is generated when used by the reaction of the acidic substance with a chlorite in the first composition. In addition, the second composition is alone in the form of gel, while the mixed composition produced by mixing it with the second composition used in the present invention is also in the form of gel and adheres to an object of interest in the form of gel to exhibit the effect of chlorine dioxide for a prolonged time.

[Acidic Substance]

The second composition contains an acidic substance. As the acidic substance used in the second composition, an acidic substance that generates chlorine dioxide by mixing it with the first composition can be used alone or in combination as appropriate. The acidic substance that can be used includes one or more selected from the group consisting of citric acid, phosphoric acid, acetic acid and hydrochloric acid. Among them, mildly acidic organic acids such as citric acid, phosphoric acid and acetic acid can be suitably used. These cannot easily erode containers or the like during storage and are also highly safe. Citric acid or the like is particularly preferable because it has a low odor during storage or use.

The concentration of the acidic substance in the second composition can be appropriately set in consideration of the degree to which chlorine dioxide is generated during use. For example, the mass ratio of the acidic substance to the entire second composition (the mass of the chlorite/the mass of the first composition) can be approximately 0.5 to 20% by mass. Preferably, it may be 1 to 10% by mass or 2 to 5% by mass.

The second composition also comprises fumed silica. This fumed silica can be used in the same manner as the fumed silica comprised in the first composition described above. Hydrophobic fumed silica is preferably used also in the second composition.

The proportion of fumed silica comprised in the second composition can be appropriately set in consideration of the degree of gelation during storage and use, or the like. For example, the mass ratio of fumed silica to the entire second composition (the mass of fumed silica/the mass of the second composition) can be approximately 0.5 to 30% by mass. This lower limit may be preferably 1% by mass or more or 2% by mass or more. This upper limit may be 25% by mass or less or 20% by mass or less, depending on the gel-like viscosity thereof or the like due to the other components in the composition or the like. It is may be 15% by mass or less or 10% by mass or less because gelation easily occurs by using in combination with an alcohol, or the like.

The dispersion medium for the second composition to be used can be the same dispersion medium as that for the first dispersion medium. Therefore, a mixture produced by mixing water, isopropyl alcohol or the like as appropriate is preferably used as the dispersion medium. The pH of the second composition is substantially determined by the acidic substance, but when the pH is adjusted, the pH is preferably 5 or less and more preferably 1 to 4.

The second composition is preferably in the form of gel at least at ordinary temperature and ordinary pressure. The gelation of the second composition makes it possible to easily mix the second composition with the first composition beyond the difference therebetween in physical properties such as viscosity. In addition, the mixed composition produced by mixing them becomes a gel-like composition so that it adheres to any area and does not easily flow. For the second composition, the lower limit of the viscosity at 25° C. may be 1,000 mPa·s or more or 5,000 mPa·s or more, for example, as measured by a rotational viscometer. If the viscosity is too high, mixing may be not easily carried out or discharging or injection may not be easily carried out. Therefore, the upper limit may be 1,000 Pa·s or less or 500 Pa·s or less.

The second composition may comprise the other component(s). For example, it may comprise a colorant to clarify where it has been used or a stabilizer, a preservative, a moisturizer, an aroma chemical or the like. In general, if it comprises a polymer-based thickener having a thickening effect, the thickener may cause strings be drawn from a discharging section (stringiness) when used. Therefore, the polymer-based thickener may be used with an upper limit of 2% by mass or less, 1% by mass or less, 0.5% by mass or less, 0.1% by mass or less or the like, so that it is not substantially contained not to cause these problems.

[Mixed Composition]

The chlorine dioxide generation device and the chlorine dioxide generation system of the present invention generate chlorine dioxide from a mixed composition produced by mixing the first composition and the second composition. This generation of chlorine dioxide occurs when a chlorite of the first composition reacts with an acidic substance in the mixed composition. The generated chlorine dioxide vaporizes at any area to which the mixed composition is adhered or on/in which it is placed and diffuses in the vicinity. With this chlorine dioxide, disinfection and the like can be carried out by killing microorganisms and viruses.

The mixing ratio of the first composition and the second composition is appropriately set in consideration of the type and concentration of each of active ingredients contained in each of the compositions, the rate and period of generation of chlorine dioxide, or the like. For example, the mass ratio of the first composition to the second composition (the first composition: the second composition) may be approximately 1:10 to 10:1. It may be preferably approximately 1:5 to 5:1 and 1:2 to 2:1.

The first composition and the second composition are mixed in a mixing section 41 or the like. In the case of a chlorine dioxide generation device 101, the first and second compositions can be mixed by kneading an outer container 31 in the vicinity of the compositions in the mixing section 41. In the case of a chlorine dioxide generation device 102, the first and second compositions are mixed by pushing a button 62 to open a connecting section between piping 121 and the piping 221 so that the gel-like compositions extruded by the pressures applied to both containers come into collision with each other. The mixed composition is discharged as a gel-like composition from a discharging section and is stably retained at the area to which it is adhered. Chlorine dioxide is generated in this area in which the composition is retained.

Generation of chlorine dioxide may be carried out by using a device or the like in which the first composition and the second composition may be subjected to mixing in a mixing section, or by using a system in which each of the compositions are previously prepared and they are then mixed and used at any area.

The chlorine dioxide generation device and the chlorine dioxide generation system of the present invention can be used by adhering a mixed composition, which becomes a gel-like composition, to any area or object for the purpose of sanitization, disinfection, sterilization, deodorization, epidemic prevention, or the like. For example, they can be used for the prevention and treatment of diseases caused by viruses and microorganisms such as colds in such places as homes, offices, hospitals, transportation facilities, facilities or factories, or they can be used for the prevention and treatment of livestock diseases in such places as animal houses.

EXAMPLES

Hereinafter, the present invention will be described in more detail with reference to Examples, but the present invention is not limited to the following Examples unless the gist of the invention is changed.

[Reagents and the Like]

Sodium chlorite: manufactured by OSAKA SODA CO. LTD.

Citric acid: manufactured by Hayashi Pure Chemical Ind., Ltd.

Fumed silica (1): "A200" manufactured by NIPPON AEROSIL CO., LTD.

Hydrophobic fumed silica (1): "RY200" manufactured by NIPPON AEROSIL CO., LTD.

Isopropyl alcohol: manufactured by Hayashi Pure Chemical Ind., Ltd.

Experimental Example 1

1) The following aqueous solution of sodium chlorite (1) and aqueous solution of citric acid (1) were prepared.

Aqueous solution of sodium chlorite (1)

Purified water (93.9% by mass), fumed silica (1) (6% by mass) and sodium chlorite (0.1% by mass) were mixed. This aqueous solution of sodium chlorite (1) had a pH of 8.8.

Aqueous solution of citric acid (1)

Purified water (90% by mass), fumed silica (1) (6% by mass) and citric acid (4% by mass) were mixed. This aqueous solution of citric acid (1) had a pH of 2.5.

2) The solutions prepared in the above 1) were placed in an aerosol can according to the chlorine dioxide generation device 102 of the second embodiment, respectively and a spray injection test was carried out. The aqueous solution of citric acid (1) had a slightly low viscosity and was thereby slightly low miscibility with the aqueous solution of sodium chlorite (1), but a mixed composition was in the form of gel and could be adhered to any area.

3) The solutions prepared in the above 1) were allowed to stand under an atmosphere of room temperature for one day, and the state of each solution was observed. The aqueous solution of sodium chlorite (1) turned yellow, and it smelled of chlorine dioxide when the container was opened. It is expected that the solution had a slightly low pH, protons were released due to the hydroxy group of fumed silica (1) and the reaction with these protons occurred.

Comparative Example 1

A spray test was carried out by using an aqueous solution of citric acid prepared by mixing 95% by mass of purified water, 1% by mass of sodium polyacrylate, and 4% by mass of citric acid instead of the aqueous solution of citric acid (1) in Experimental Example 1. That is, the spray test was carried out in the same manner as in 2) of Experimental Example 1 except that sodium polyacrylate was mixed as a thickener instead of fumed silica contained in the aqueous solution of citric acid (1) to provide the similar viscosity. The injected gel had a stringiness and was difficult to handle.

Experimental Example 2

1) The following aqueous solution of sodium chlorite (2) and aqueous solution of citric acid (2) were prepared.

Aqueous Solution of Sodium Chlorite (2)

Purified water (90.95% by mass), sodium chlorite (3% by mass), sodium hydroxide (0.05% by mass) and fumed silica (1) (6% by mass) were mixed. This aqueous solution of sodium chlorite (2) had a pH of 10.5.

Aqueous Solution of Citric Acid (2)

Purified water (90% by mass), citric acid (4% by mass) and fumed silica (1) (6% by mass) were mixed. This aqueous solution of citric acid (2) had a pH of 2.5.

2) The solutions prepared in the above 1) were placed in an aerosol can according to the chlorine dioxide generation device 102 of the second embodiment, respectively and a spray injection test was carried out. The mixed composition injected from a discharging section was a gel-like composition and adhered to the area on/in which it was injected.

In addition, it could be confirmed that chlorine dioxide was generated, and it was also confirmed that chlorine dioxide was continuously generated in an open state even after 3 days had passed.

3) The solutions prepared in the above 1) were allowed to stand under an atmosphere of room temperature for one day, and the state of each solution was observed. No abnormalities in appearance were observed in both the solutions.

Experimental Example 3

1) The following aqueous solution of sodium chlorite (3) and aqueous solution of citric acid (3) were prepared.

Aqueous Solution of Sodium Chlorite (3)

Purified water (45.45% by mass), isopropyl alcohol (45.5% by mass), sodium chlorite (3% by mass), sodium hydroxide (0.05% by mass) and hydrophobic fumed silica (1) (6% by mass) were mixed. This aqueous solution of sodium chlorite (3) had a pH of 10.5.

Aqueous Solution of Citric Acid (3)

Purified water (45% by mass), isopropyl alcohol (45% by mass), citric acid (4% by mass) and hydrophobic fumed silica (1) (6% by mass) were mixed. This aqueous solution of citric acid (3) had a pH of 2.0.

Both the aqueous solution of sodium chlorite (3) and the aqueous solution of citric acid (3) had a viscosity of about 200 Pa·s.

Figure 4:
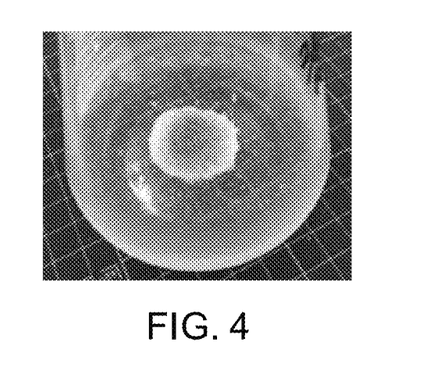
FIG. 4 is a diagram showing a gel of a mixed composition generating chlorine dioxide, injected by a chlorine dioxide generation device according to the present invention.

2) The solutions prepared in the above 1) were placed in an aerosol can according to the chlorine dioxide generation device 102 of the second embodiment, respectively and a spray injection test was carried out. The mixed composition injected from a discharging section was a gel-like composition and adhered to the area on/in which it was injected. This gel-like composition stably adhered to the area on/in which it was injected, without causing dripping or the like. The state of the injected gel-like composition is shown in FIG. 4. The mixed composition of Experimental Example 3 in which hydrophobic fumed silica (1) was used remained more stably on the adhered object than that of Experimental Examples 1 and 2 in which fumed silica (1) was used.

In addition, it could be confirmed that chlorine dioxide was generated, and it was also confirmed that chlorine dioxide was continuously generated in an open state even after 3 days had passed.

3) The solutions prepared in the above 1) were allowed to stand under an atmosphere of room temperature for one day, and the state of each solution was observed. No abnormalities in appearance were observed in both the solutions.

INDUSTRIAL APPLICABILITY

The chlorine dioxide generation device and the chlorine dioxide generation system of the present invention are industrially useful, because they can be utilized by adhering a gel-like composition for the purpose of sanitization, disinfection, sterilization, deodorization and epidemic prevention.

REFERENCE SIGNS LIST 101, 102, 103 chlorine dioxide generation device
11, 12 first container
13 inner container
121, 221 piping
21, 22 second container
31, 32, 33 outer container
41, 42, 43 mixing section
51, 52, 53 discharging section
61, 63 notch
62 button

The invention claimed is:
1. A chlorine dioxide generation device, comprising:
a first container containing a first composition comprising a chlorite and fumed silica, and water and/or an alcohol as a dispersion medium;

a second container containing a second composition comprising an acidic substance and fumed silica, and water and/or an alcohol as a dispersion medium;

an outer container housing the first container and the second container;

a mixing section that mixes the first composition released from the first container and the second composition released from the second container to produce a mixed composition; and a discharging section that discharges the mixed composition produced by mixing in the mixing section.

2. The chlorine dioxide generation device according to claim 1, wherein:

the first container and the second container are bag-shaped;

the outer container is a pressure-resistant container that houses the first container and the second container and is filled with a propellant;

the mixing section is a joint section of piping connected to the first container housed in the pressure-resistant container and piping connected to the second container housed in the pressure-resistant container;

the chlorine dioxide generation device comprises an on-off valve for adjusting the release of the first composition and the second composition to the mixing section and the discharging section; and the mixed composition is injected from the discharging section by opening the on-off valve.

3. The chlorine dioxide generation device according to claim 1, wherein the fumed silica is a hydrophobic fumed silica.

4. The chlorine dioxide generation device according to claim 1, wherein the chlorite is one or more selected from the group consisting of sodium chlorite, potassium chlorite and calcium chlorite.

5. The chlorine dioxide generation device according to claim 1, wherein the acidic substance is one or more selected from the group consisting of citric acid, phosphoric acid, acetic acid and hydrochloric acid.

6. The chlorine dioxide generation device according to claim 1, wherein a pH of the first composition is 9 or more.

7. The chlorine dioxide generation device according to claim 1, wherein the first composition contains one or more selected from the group consisting of sodium hydroxide, potassium hydroxide, lithium hydroxide, calcium hydroxide, magnesium hydroxide, sodium carbonate and sodium tetraborate.

8. The chlorine dioxide generation device according to claim 1, wherein a pH of the second composition is 5 or less.

9. A chlorine dioxide generation device, comprising:

a first composition comprising a chlorite and fumed silica, and water and/or an alcohol as a dispersion medium;

and a second composition comprising an acidic substance and fumed silica, and water and/or an alcohol as a dispersion medium; wherein:

the chlorine dioxide generation device comprises:

an inner container containing any one composition of the first composition and the second composition; and an outer container containing the other composition that is not contained in the inner container, the inner container being included in the outer container; and the chlorine dioxide generation device comprises:

a mixing section that mixes the one composition released from the inner container and the other composition contained in the outer container to produce a mixed composition; and a discharging section that discharges the mixed composition produced by mixing in the mixing section.

10. A chlorine dioxide generation system, comprising a first composition comprising a chlorite and fumed silica, and water and/or an alcohol as a dispersion medium; and a second composition comprising an acidic substance and fumed silica, and water and/or an alcohol as a dispersion medium, wherein chlorine dioxide is generated from a mixed composition produced by mixing the first composition and the second composition.

* * * * *